United States Patent [19]

Mittleman

[11] 4,388,593
[45] Jun. 14, 1983

[54] COIL DEVICE FOR UNDERWATER MAGNETIC TESTING

[75] Inventor: John Mittleman, Panama City, Fla.

[73] Assignee: The United States of America as represented by the Secretary of the Navy, Washington, D.C.

[21] Appl. No.: 206,424

[22] Filed: Nov. 13, 1980

[51] Int. Cl.³ .................. G01R 33/12; G01N 27/84; H01F 5/04

[52] U.S. Cl. .................. 324/262; 324/216; 324/228; 336/20

[58] Field of Search .................. 324/200, 214–218, 324/226, 228, 232, 234–243, 260, 262; 336/20

[56] References Cited

U.S. PATENT DOCUMENTS

| 2,060,458 | 11/1936 | Billstein | 324/217 X |
| 2,439,827 | 4/1948 | Sterenbuch et al. | |
| 2,629,002 | 2/1953 | Tinker | 324/54 |
| 2,650,344 | 8/1953 | Lloyd | 324/232 |
| 2,895,103 | 7/1959 | Vogt et al. | 324/260 |
| 3,500,181 | 3/1970 | Jackson | 324/238 |
| 3,523,241 | 8/1970 | Barton | 324/260 |

FOREIGN PATENT DOCUMENTS

| 844131 | 6/1970 | Canada | 324/228 |
| 1197640 | 7/1970 | United Kingdom | 324/262 |
| 744220 | 6/1980 | U.S.S.R. | 324/237 |

Primary Examiner—Gerard R. Strecker
Attorney, Agent, or Firm—Richard S. Sciascia; Harvey A. David

[57] ABSTRACT

A coil device for use by divers in subjecting an elongate underwater structure member to a magnetic field for inspection purposes includes a framework supporting a winding having first and second coaxial coils of predetermined coil diameter that lie in substantially parallel planes separated axially by a distance at least twice the coil diameter, the coils being electrically connected in series so as to generate magnetic fields of opposite polarity. The coils, connecting conductors, and framework are adapted to be spread open and closed around the member to be inspected.

6 Claims, 4 Drawing Figures

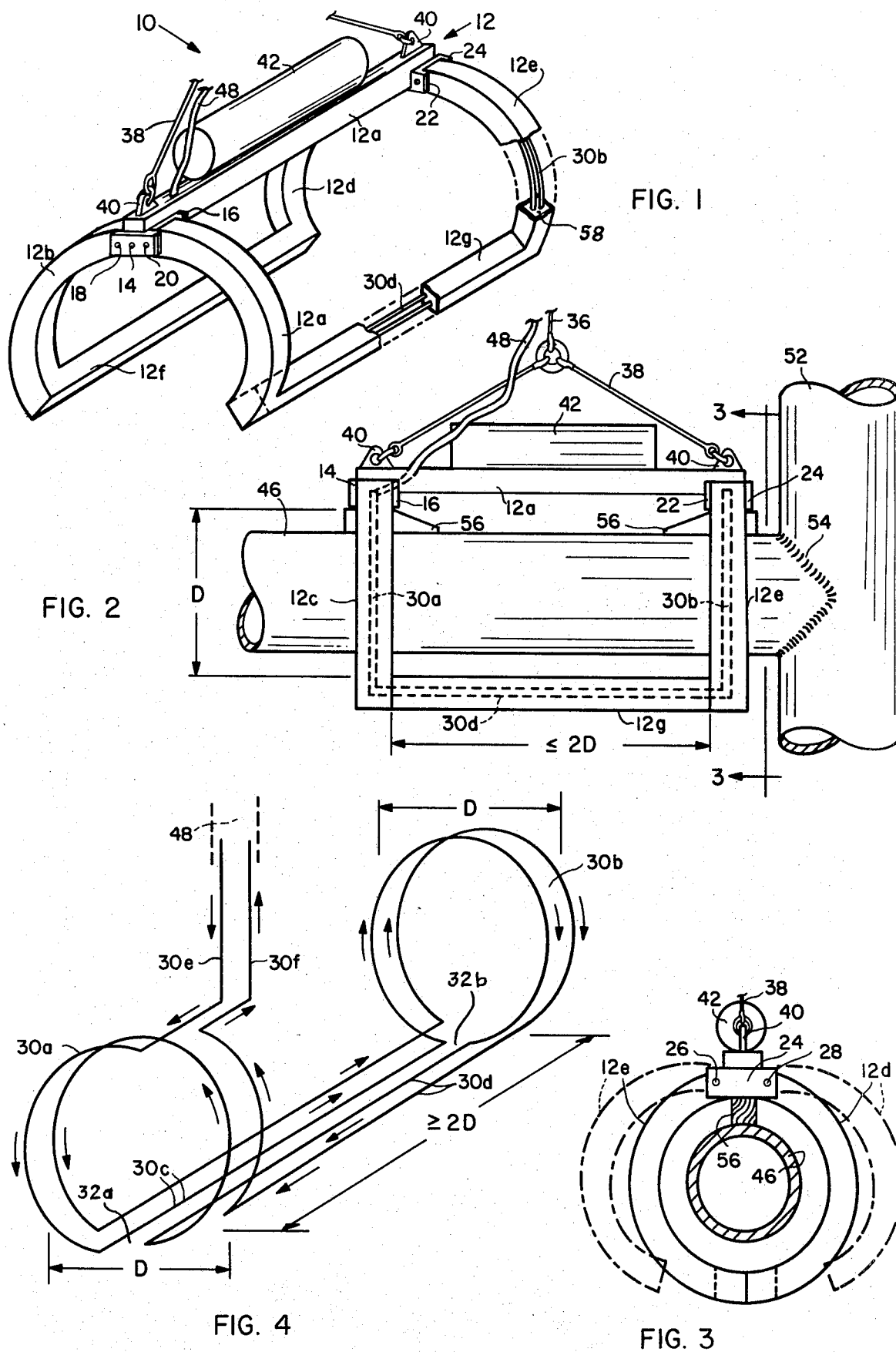

COIL DEVICE FOR UNDERWATER MAGNETIC TESTING

BACKGROUND OF THE INVENTION

This invention relates to apparatus for use in magnetic inspection or testing procedures, and more particularly to devices especially suited to use in magnetic detection of faults in members or joints between members forming part of underwater structures.

The art of performing magnetic inspection tests on ferromagnetic structural members, particularly those tests wherein a member is subjected to a magnetic flux so that orientations of a plurality of magnetic particles can be observed as indicative of any of a variety of faults, has been extensively used. In the case of elongated test members, such as structural beams, tubes, or pipes, the magnetic flux has typically been induced in the member by means of an electrically energized coil or solenoid about the member, by application of permanent magnets to the member adjacent the zone to be inspected, or by causing a high amperage current to flow in the test member by application of current prods adjacent the weldment or other zone to be inspected. Where it is desired to use the electrical coil approach and the member is of substantial length or an end is inaccessible, it has been necessary to either manually wrap or wind a coil about the member or to use separable coil structures such as are illustrated in U.S. Pat. No. 2,439,827 to H. Sterenbuch, et al, and U.S. Pat. No. 2,895,103 to E. Vogt, et al.

While those expedients and devices are reasonably satisfactory for inspection and test procedures made under ordinary circumstances, they have been found to have serious shortcomings and disadvantages for use by divers in testing or inspection of underwater structures. In the case of manually wrapping a flexible cable around the test member, it is necessary for the diver to either make an underwater electrical connection of the free end to a power supply line or to have the free end hoisted to the surface for connection above water. The use of underwater connections has been found troublesome and dangerous to the safety and health of the diver, and the hoisting of the free end to the surface for each test requires that the diver handle inordinate lengths of cable in making the wrap. The mentioned separable coil devices, because of their make and break contacts or connections to form each coil turn, are wholly unsatisfactory for underwater use because of the conductive nature of the water medium, especially in the case of salt water and the fact that they may have to carry several hundred amperes of current. Both magnetic probes and current prods are limited because they produce only very localized magnetic fields rather than a predictable field throughout a weldment. Also, current prods, which typically transmit 1000 amperes or more, through bare contacts, present an extreme hazard to the diver and may cause deterioration of the steel member being inspected if arcing between the prod and the steel member occurs. Magnetic probes are, of course, less hazardous but may be unsuited to the particular geometries concerned. For example, the diver may be unable to inspect portions of a weld which lie in the acute angle formed between intersecting pipes or members of an underwater structure.

SUMMARY OF THE INVENTION

With the foregoing in mind, it is a principle object of this invention to provide a new and useful apparatus or device for carrying out magnetic inspection or testing of steel or other ferromagnetic structural members in an underwater environment.

Another important object is the provision of an electrically energizable magnetic flux generating coil device that can be easily and safely handled underwater by a diver and which will pose no hazards of electrical nature to the diver when the device is energized.

As another object the invention aims to provide a magnetic testing device for the foregoing character that can readily be applied to elongated structural members without access to an end thereof, and which can be used to generate an electrical flux in a joint or weldment of intersecting members.

Still another object is the provision of a magnetic flux testing coil device that is relatively inexpensive, reliable in operation, and requires no underwater electrical make and break connections or bare electrical elements.

Other objects and many of the attendant advantages will be readily appreciated as the subject invention becomes better understood by reference to the following detailed description, when considered in conjunction with the accompanying drawings.

DESCRIPTION OF THE DRAWINGS

FIG. 1 is a perspective illustration of a coil device embodying the invention for underwater magnetic testing;

FIG. 2 is a side elevational view of the device of FIG. 1 shown in association with an underwater structure undergoing test.

FIG. 3 is a sectional view taken substantially along line 3—3 of FIG. 2; and

FIG. 4 is a perspective illustration diagrammatically illustrating the electrical coil configuration of the device of FIG. 1.

DESCRIPTION OF THE PREFERRED EMBODIMENT

Referring now to FIG. 1 of the drawings, a magnetic coil device 10 representing the presently preferred embodiment of the invention comprises an electrical coil supporting framework, indicated generally at 12. The framework 12, is advantageously formed of a light weight, non-magnetic material such as aluminum or a suitable water resistant synthetic plastic, and comprises a strongback or spreader bar 12a, a first pair of arcuate coil form segments 12b and 12c at one end of the spreader bar, and a second pair of arcuate coil form segments 12d and 12e at the other end thereof.

The segments 12b and 12c lie in a first plane substantially normal to the spreader bar 12a, and are hinged or pivoted for swinging movement relative to one another in that plane. This is conveniently accomplishd by providing a pair of spaced, parallel hinge plates 14, 16 fixed at the end of the bar 12a, between which the coil form segments 12b and 12c are pivotally connected as at 18 and 20.

Similarly, the segments 12d and 12e lie in a second plane substantially normal to the spreader bar 12a, and are hinged or pivoted for swinging movement relative to one another in that second plane. A second pair of spaced, parallel hinge plates 22 and 24 are fixed at the corresponding other end of the bar 12a, between which the segments 12d and 12c are pivotally connected as at 26 and 28.

The arcuate coil form segments 12b, 12c, 12d, and 12 are channel shaped in section in order to receive an electrical winding which is generally indicated at 30 in FIG. 4 and will presently be described more fully. The framework 12 further comprises a pair of longitudinally extending channel members 12f and 12g interconnecting the pairs of coil form segments. Thus, channel member 12f connects the otherwise free end of the segment 12b with the corresponding end of the segment 12d so that those segments are adapted to swing in unison about their respective pivots. Similarly, channel member 12g interconnects the otherwise free ends of the segments 12c and 12e. The channel members 12f and 12g contain portions of the winding 30.

The device 10 is adapted to be lowered to or hoisted from a diver's work site by means of a suitable hoist line 36 and bridle 38 connected to eyes 40 at opposite ends of the spreader bar 12a. A buoyancy chamber 42 is fixed to the bar 12a in order to reduce the negative buoyancy of the device 10 to a value that permits easy handling and positioning of the device by a diver.

Referring additionally now to FIGS. 2 and 3, it will be appreciated that the device 10 is readily positioned about a structural member, such as a pipe 46 by lowering the device over the pipe with the coil form segments 12b, 12c, 12d, and 12e in their opened position of FIG. 1, after which the segment pairs are closed as is best shown in FIG. 3.

The geometry or configuration of the winding 30, which is conveniently formed of flexible, electrically insulated, conductive wire, is best illustrated in FIG. 4. It will be seen that the winding comprises a first solenoid coil 30a and a second coil 30b lying in spaced, coaxial, parallel relation and connected by axially extending conductors 30c and 30d. These coils are characterized by radial gaps or openings 32a, 32b into the interior thereof.

The spacing of the coils 30a, 30b from one another is at least about equal to or greater than twice the effective diameter D of the coils.

The winding 30 is served by input and output conductors 30e, 30f, conveniently combined into a suitably protected power supply line 48 for connection to a source of electrical current at the surface. The directions of current current flow when the winding 30 is energized with direct current, or at a particular instant when energized with alternating current, are indicated by the arrows adjacent various portions of the winding. It will be recognized that the coil 30a will induce a magnetic flux in the portion of the pipe 46 of opposite polarity to that induced in the portion of the pipe within the coil 30b.

Because the axial flux generated by a solenoid coil falls off substantially within two coil diameters the separation of the coils precludes interference of either coil with the flux induced by the other in the pipe on the sides of the coils facing away from the device. Accordingly, with the device 10 disposed as illustrated in FIG. 2 on the structural member 46, and with one coil, e.g., 30b, disposed adjacent a structural node or joint such as the intersection of pipe member 46 with a pipe member 52, a substantial magnetic flux can be set up in the weldment 54 as a zone for magnetic particle inspection. The actual inspection is carried out in a manner well known to those skilled in the art to which the invention pertains and need not be fully explained herein. Suffice it to say that the application of magnetic particles, or a substance containing such particles, allows a skilled person to determine a variety of conditions concerning the inspected zone.

The inside diameters of the arcuate segments 12b, 12c, 12d, and 12e, may be selected to permit closure of the device about members in a selected range of outer diameters. When a member to be inspected is less than the maximum that can be accommodated by the device 10, spacer means, such as wedges 56 of wood, aluminum, or other suitable material may be used to substantially center the device relative to the test member.

The winding 30 is secured by potting 58 or other suitable means in the channel shaped portions of the framework 12 in which it lies, except for the areas between the hinge plates where flexure of the wires is required.

For some applications, for example where it is desirable to perform inspections at joints adjacent a bend or angle in the structural member, one or both of the coils and supporting curved frame segments may be of eliptical rather than circular configuration. Additionally, in circumstances wherein the added strength and/or flotation are unnecessary, the spreader bar 12a and/or the flotation chamber 42 may be omitted.

Obviously, other embodiments and modifications of the subject invention will readily come to the mind of one skilled in the art having the benefit of the teachings presented in the foregoing description and the drawing. It is, therefore, to be understood that this invention is not to be limited thereto and that said modifications and embodiments are intended to be included within the scope of the appended claims.

What is claimed is:

1. A magnetic coil device for use under water in magnetic particle inspection of structural members, said device includng an electrical winding and characterized by the improvement wherein said winding comprises:
   first and second substantially annular, coaxially spaced electrically conductive solenoid coils each having a predetermined diameter and each characterized by a radial discontinuity aligned with the discontinuity of the other;
   first and second axially extending conductor means connecting conductor portions of one of said coils in alternate sequence with conductor portions of the other coil for simultaneous series energization whereby substantially annular current flow occurs in one direction at any instant in all said conductor portions of one of said coils and occurs in the opposite direction in all said conductor portions in the other of said coils;
   said coils being flexible, at least in part, whereby said coils can be spread open and closed at said discontinuities to permit placement around an elongate structural member;
   conductor lead means for energizing said winding from a remote electrical power source; and
   support means for maintaining said coils coaxially spaced and supporting said winding relative to a structural member being inspected.

2. A coil device as defined in claim 1, and wherein:
   said first and second coils are oriented so as to provide first and second magnetic fields of opposite polarity; and
   said first and second coils are axially spaced apart and predetermined distance about equal to or greater than twice said predetermined coil diameter, whereby said first and second magnetic fields are characterized by a flux density, on the outer side of each coil, that is substantially unaffected by the field of the other coil.

3. A coil device as defined in claim 2, an wherein:
each of said first and second coils comprises a plurality of turns and said coils, said axially extending conductor means, and said conductor lead means are all formed of a single, continuous, insulated, electrical conductor.

4. A magnetizing coil device for use underwater in magnetic particle inspection of elongate structural members, said device comprising:
a winding supporting framework comprising a longitudinal strongback of predetermined length, first and second arcuate frame segments supported from one end of said strongback for swinging movement between open positions for passing over a structural member to be tested and closed positions substantially encircling said structural member, third and fourth arcuate frame segments supported from the opposite end of said strongback for swinging movement between corresponding open and closed positions, a first longitudinal frame segment interconnecting the outer ends of said first and third arcuate frame segments for movement in unison, and a second longitudinal frame segment interconnecting the outer ends of said second and fourth arcuate frame segments for movement in unison; and
a winding supported by said framework and comprising a single conductor of which a plurality of first portions are configured into a first substantially annular coil of predetermined diameter supported by said first and second arcuate segments, a plurality of second portions of said conductor being configured into a second substantially annular coil of like diameter supported by said third and fourth arcuate frame segments, said coils each having a gap located diametrically opposite said strongback and variable in size through which said member to be tested can pass when said arcuate frame segments are in said open positions, said gaps being substantially closed when said arcuate frame segments are in their closed positions, said first and second portions of said conductor being interconnected in alternating series relation by a plurality of longitudinally extending portions of said conductor supported on opposite sides of said gaps by said first and second longitudinal frame segments, so that all conductor portions of said first coil are operative, when said winding is energized, to carry current in the same annular direction of flow at the same time while all conductor portions of said second coil are operative to carry said current in the opposite annular direction of flow at said same time, whereby said first and second coils create axially spaced first and second magnetic flux zones of opposite field polarities in the member to be tested.

5. A device as defined in claim 4, and wherein:
said first and second coils have a predetermined inside diameter; and
said predetermined length of said strongback is such that the said first and second coils are spaced apart by a distance of at least about twice said predetermined inside diameter.

6. A device as defined in claim 5, and wherein:
said framework comprises buoyancy means mounted on said strongback for reducing negative buoyancy of said device.

* * * * *